United States Patent
Evertsz et al.

(10) Patent No.: US 7,672,495 B2
(45) Date of Patent: Mar. 2, 2010

(54) METHOD, APPARATUS AND COMPUTER PROGRAM FOR DISPLAYING MARKS IN AN IMAGE DATA SET

(75) Inventors: Carl J. G. Evertsz, Bremen (DE); Anke Bodicker, Bremen (DE); Sriram Krishnan, Exton, PA (US); Balaji Krishnapuram, Phoenixville, PA (US); R. Bharat Rao, Berwyn, PA (US); Dennis O'Dell, Phoenixville, PA (US); Alok Gupta, Bryn Mawr, PA (US)

(73) Assignee: MeVis BreastCare GmbH & Co. KG, Bremen (DE)

( * ) Notice: Subject to any disclaimer, the term of this patent is extended or adjusted under 35 U.S.C. 154(b) by 0 days.

(21) Appl. No.: 11/465,386

(22) Filed: Aug. 17, 2006

(65) Prior Publication Data

US 2008/0044068 A1 Feb. 21, 2008

(51) Int. Cl.
*G06K 9/00* (2006.01)
(52) U.S. Cl. .................................... 382/128
(58) Field of Classification Search ............... 382/128; 128/922; 600/410–422
See application file for complete search history.

(56) References Cited

U.S. PATENT DOCUMENTS

| | | | |
|---|---|---|---|
| 6,075,879 A | | 6/2000 | Roehrig et al. |
| 7,298,877 B1 * | | 11/2007 | Collins et al. ............... 382/128 |
| 2001/0043729 A1 | | 11/2001 | Giger et al. |
| 2003/0227468 A1 | | 12/2003 | Takeda |
| 2005/0010445 A1 | | 1/2005 | Krishnan et al. |
| 2005/0069184 A1 * | | 3/2005 | Kasai ........................ 382/128 |
| 2006/0164511 A1 | | 7/2006 | Krupnik |
| 2006/0215894 A1 * | | 9/2006 | Lakare ....................... 382/128 |
| 2006/0274928 A1 * | | 12/2006 | Collins et al. ............... 382/132 |
| 2007/0274585 A1 * | | 11/2007 | Zhang et al. ................. 382/132 |

OTHER PUBLICATIONS

U.S. Appl. No. 11/465,078, filed Aug. 16, 2006, entitled "Method, Apparatus and Computer Program for Presenting Cases Comprising Images," inventor: Carl J. G. Evertsz et al.
U.S. Appl. No. 11/465,074, filed Aug. 16, 2006, entitled "Presentation Method, Presentation Device and Computer Program for Presenting an Image of an Object," inventor Carl J. G. Evertsz et al.
Zhou, C. et al., "Computerized Nipple Identification for Multiple Image Analysis in Computer-Aided Diagnosis," Medical Physics, vol. 31, No. 10, Oct. 2004, pp. 2871-2882.

* cited by examiner

*Primary Examiner*—Brian P Werner
*Assistant Examiner*—Katrina Fujita
(74) *Attorney, Agent, or Firm*—Black Lowe & Graham PLLC

(57) ABSTRACT

A method and an apparatus display marks in an image data set, wherein an image data set comprising marks is provided and wherein during a review phase not all marks within the image data set are displayed at the same time. A list of the marks can be generated by sorting the marks depending on a predetermined sorting criterion and wherein the marks are displayed temporally one after another within the image data set in accordance with the generated list. The image data set is for example a medical image data set, wherein the marks are computer-aided detection (CAD) marks and wherein the sorting criterion is the probability of marking illness, in particular the suspiciousness.

23 Claims, 8 Drawing Sheets

METHOD, APPARATUS AND COMPUTER PROGRAM FOR DISPLAYING MARKS IN AN IMAGE DATA SET

TECHNICAL FIELD

This disclosure generally relates to a method, an apparatus and a computer program for displaying marks in an image data set.

BACKGROUND INFORMATION

Image data sets are in general generated by image generation devices. These image generation devices are, for example, mammography scanners, computed tomography scanners, magnetic resonance imaging scanners and ultra sound scanners, which are, in particular, used for diagnostic purposes. The generated image data sets are often transferred to marks generation devices, like a computer-aided-detection device (CAD device), for determining marks indicating certain locations within the image data sets. For example, in the case of a medical image data set, the CAD device can determine marks indicating locations within the image data set, which are suspicious of showing cancer. In this case, a user, like a radiologist, could examine the locations within the image data set indicated by the marks, in order to determine, whether cancer is present or not.

Such an image data set comprises often a large amount of marks, whereby a viewer, for example, a radiologist, can be confused and might overlook important or suspicious marks.

It is known to visualize the marks within the image data set with variable size. It is, for example, known to visualize marks of higher importance, e.g. of higher suspiciousness of marking cancer, with a larger size than marks having a smaller importance in order to draw the attention of a user to the most important marks. But there are still a lot of marks present in the image data set having different sizes, wherein a user, like a radiologist, can still be confused. Furthermore, if the computer program, which is used to determine the importance of a mark, like a CAD computer program of a CAD device, does not correctly determine the importance of a mark, this mark is visualized with a smaller size and the probability of overlooking an important mark is even increased.

BRIEF SUMMARY OF THE INVENTION

Embodiments of the present invention provide a method, an apparatus and a computer program for displaying marks in an image data set, which display the marks in an image data set such that the marks within the image data set are clearly shown, without confusing a user, like a radiologist, decreasing the probability of overlooking important marks.

In a first aspect of the present invention a method for displaying marks in an image data set is presented, wherein an image data set comprising marks is provided and wherein during a review phase not all marks within the image data set are displayed at the same time.

One embodiment of the invention is based on the idea, that, if less marks are shown within the image data set at the same time, a user is less confused and the probability of overlooking an important mark is decreased.

It is preferred in one embodiment that a list of marks is generated by sorting the marks depending on a predetermined sorting criterion and that the marks are displayed temporally one after another during the review phase within the image data set in accordance with the generated list. In this embodiment, during the review phase only one mark is shown at the same time within the image data set, e.g., the users' attention is completely drawn to each mark, further reducing the probability of overlooking an important mark. Furthermore, since the marks are shown in a sorted way, it is possible to show the marks in a sequence, which suits to a certain application. For example, the sorting criterion could be the importance of a mark with respect to a certain application, e.g. the suspiciousness of marking cancer in the case of medical image data sets, and the list can be generated such that the most important marks are shown first, since the attention of the user might be higher at the beginning of a review of the marks than at the end. The sorting criterion can, for example, be predetermined by inputting a sorting criterion by a user, like a radiologist, into an apparatus for displaying marks in an image data set, which is adapted to perform the method in accordance with one embodiment of the invention.

It is further preferred in one embodiment that the image data set is a medical image data set, for example, a set of digital mammograms, that the marks are CAD marks and that the sorting criterion is the probability of marking illness, in particular the suspiciousness. The medical image data set can, for example, also be a tomosyntheses image data set, a computed tomography image data set, a breast magnetic resonance imaging data set or any other medical image data set. In this case, the importance of a mark is correlated with the probability of marking illness, e.g., a mark having a higher probability of marking illness has a higher importance than a mark having a lower probability of marking illness. The illness is, for example, cancer. The suspiciousness is a well defined CAD term and is, for example, provided by a CAD mark generation device and a CAD mark generation computer program. A CAD mark generation device using a CAD mark generation computer program is, for example, the Image Checker System produced by R2 Technology Inc. or the Second Look Digital System produced by iCAD Inc. The suspiciousness is a part of the DICOM standard, in particular, the suspiciousness is a part of the DICOM CAD Structure Report (SR), which is, for example, disclosed in Digital Imaging and Communications in Medicine (DICOM) 2006, published by the ACR (the American College of Radiology) and the NEMA (the National Electrical Manufacturers Association), in particular, in DICOM Base Standard 2006 Part PS 3.16; Supplement 50: Mammography Computer-Aided Detection SR SOP. The SR is, for example, generated by the above mentioned CAD mark generation device and CAD mark generation computer program.

Since in the above mentioned embodiment the marks are sorted in accordance with their probability of marking illness and since they are shown in this sequence temporally one after another, the marks can be presented to the user, like a radiologist, in accordance with the actual level of attention of the user. For example, if the user has the highest attention at the beginning of a review of the marks, the marks will be sorted such that the first shown marks have the highest probability of marking illness. If, for example, the attention of the user reaches the maximum in the middle of the review of the marks, the marks can be sorted such that the mark with the highest probability of marking illness are arranged in the middle of the generated list. Thus, the probability of marking illness of the CAD marks can be adapted to the attention of the user, further decreasing the probability of overlooking important marks.

It is preferred in one embodiment that the next mark in the generated list is displayed after fulfilling a predetermined switching criterion. The predetermined switching criterion is, for example, an input to an apparatus for displaying marks in an image data set, which performs the method in accordance with one embodiment of the invention. The apparatus for displaying marks in an image data set can comprise an input device, for example, a keyboard or a mouse, for inputting a signal indicating that the next mark can now be shown. Thus, in this example, the switching criterion is an input criterion, e.g., whether a signal has been inputted indicating that the next mark can now be shown or whether such a signal has not been inputted. Thus, a user can review a mark within the image data set as long as needed and, after the user has reviewed the respective mark, the user can switch to the next mark. This further decreases the probability of overlooking an important mark and of a misassessment of a mark, in particular, of generating a false negative or a false positive.

It is further preferred in one embodiment that an indication is displayed indicating the position of the displayed mark within the list and/or the overall number of marks to be displayed. This allows the user to see directly how many marks have already been displayed and how many marks will be displayed. Furthermore, since the marks are sorted in dependence on a predetermined sorting criterion, this allows to give the user an impression of the importance of the displayed mark. For example, if the sorting criterion is the probability of marking illness, the position of the displayed marks within the list gives the user an impression of the probability of marking illness of the displayed mark.

It is further preferred in one embodiment that the method comprises following steps:
  generating a list of the marks by sorting the marks depending on a predetermined sorting criterion,
  grouping the marks into groups wherein each group contains marks being successive in the generated list,
  displaying the groups temporally one after another within the image data set during the review phase.

In this embodiment, groups of marks being successive in the generated list are shown at the same time. This allows to review several marks, which might be similar with respect to the sorting criterion, at the same time, wherein the speed of reviewing is increased, while, since only groups and not all markers are shown, the user is still not confused by the amount of marks displayed at the same time.

Also, if groups of marks are displayed within the image data set temporally one after another, it is preferred in one embodiment that the image data set is a medical image data set, that the marks are CAD marks and that the sorting criterion is the probability of marking illness, in particular, the suspiciousness. Furthermore, also in this case, it is preferred in one embodiment that the next group is displayed after fulfilling a predetermined switching criterion.

It is further preferred in one embodiment that only marks are displayed fulfilling at least one given displaying criterion. This at least one given displaying criterion can, for example, be the size of a mark, e.g., only marks are displayed having a size larger than a predetermined threshold value. This reduces the amount of marks, which are displayed at the same time within the image data set, whereby the probability of overlooking important marks is decreased. It is further preferred in one embodiment that the image data set is a medical image data set, that the marks are CAD marks and that the at least one given displaying criterion is at least one of a microcalcification criterion, a mass criterion and an operating point criterion. This at least one given displaying criterion can be predefined and/or inputted by a user into an apparatus for displaying marks in an image data set, which is adapted to perform the method in accordance with one embodiment of the invention.

As mentioned above, the CAD marks are provided by CAD mark generation devices and CAD mark generation computer programs, which are known in the state of the art. These devices and computer programs provide a SR, which is defined in the DICOM standard and which contains information about each CAD mark. This information describes, in particular, whether a CAD mark is a microcalcification mark or a mass mark. If a CAD mark is a microcalcification mark, this CAD mark fulfils the microcalcification criterion. If a CAD mark is a mass mark, this CAD mark fulfils the mass criterion. Two displaying criterions can be present, e.g., for example, the number of microcalcification marks and the number of mass marks can be adjusted independently. If a microcalcification criterion and a mass criterion are given, for example, inputted by a user in an apparatus for displaying marks in an image data set, which is adapted to perform the method in accordance with one embodiment of the invention, marks are displayed fulfilling both criterions, e.g., microcalcification marks and mass marks are displayed. If only one of these criterions is given, only microcalcification marks or mass marks are displayed, respectively.

The operating point is the operating point of the CAD algorithm used by the CAD mark generation device and CAD mark generation computer program. The operating point of the CAD algorithm, which has been used for determining the respective CAD mark, is also contained in the information of the SR provided from the CAD mark generation device and CAD mark generation computer program. The operating point is a measure for the probability of the determination of false positives and false negatives by the CAD algorithm. The operating point criterion is fulfilled for a respective CAD mark, if the operating point of this respective CAD mark is equal to a given operating point. The given operating point can be given by a user, which inputs the operating point via an input device, like a keyboard or a mouse, to an apparatus for displaying marks in an image data set for performing the method in accordance with one embodiment of the invention. Furthermore, the operating point can also be predetermined. The operating point is, for example, described in the section "Correction Items—By Number", CP 624 of the DICOM Standard.

The user can select via the input device, that only CAD marks are displayed which fulfil the microcalcification criterion, e.g., that only microcalcification marks are shown. Since microcalcification marks are known to be determined by the CAD algorithm with a high performance (e.g., high specificity and high sensitivity), the use of microcalcification marks for reviewing marks of an image data set can further improve a diagnosis based on this review.

The user can select via the input device, that only CAD marks are displayed which fulfil the mass criterion, e.g., that only mass marks are shown. Since CAD algorithms determine in general mass marks with a large number of false positives, it is particularly important to review these mass marks carefully. Therefore, particularly during reviewing mass marks the present invention, which assists a user, like a radiologist, in focussing on, in this embodiment, mass marks, is very useful. The user can select the mass criterion as the display criterion by inputting a corresponding signal into the apparatus for displaying marks in an image data set via an input device. If the apparatus receives such a signal, only mass marks are displayed. And, if the user has chosen a certain operating point by inputting a signal into the apparatus via the input device indicating this certain operating point, only marks are displayed belonging to this certain operating point. Since the operating point is a measure for the probability of a mark of being a false negative or false positive, by choosing a certain operating point the user can show marks having a certain probability of being a false positive or false negative.

It is preferred in one embodiment that an input device is provided for entering at least one displaying criterion as the at least one given displaying criterion in an apparatus for displaying marks in an image data set. This allows to change the number of displayed marks based on user interaction.

It is preferred in one embodiment that the marks are displayed at least in a first display area and in a second display area, wherein in both display areas one or several marks are displayed within the image data set and wherein in the second display area a region around the one or several marks is displayed with a larger magnification than in the first display area. Since in the second display area a region around the one or several marks is displayed with a larger magnification than in the first display area, the marks, e.g., the region within the image data set, which is marked by the respective mark, can be reviewed in more detail, whereby the probability of a misassessment is reduced. Furthermore, since the magnification is shown, in particular, automatically and at the same time, at which the corresponding mark is shown in the first display area, both, an overall view and a magnification, are shown at the same time, wherein a further interaction of the user for obtaining such a magnification is not needed, decreasing the time needed for reviewing the marks.

As already mentioned above, the image data set is preferentially a medical image data set in one embodiment, and the marks are preferentially CAD marks in one embodiment. The image data set is preferentially a mammogram data set in one embodiment, for example, for each breast of a patient a craniocaudal (CC) view image and a mediolateral oblique (MLO) view image, e.g., a mammogram data set comprises preferentially four images in one embodiment, a left and a right CC image, and a left and a right MLO image. It is preferred in one embodiment that a displayed mark is selected, in particular, to be discarded. For example, if, as described above, the marks are shown temporally one after another or groups of marks are shown temporally one after another, a displayed mark can be selected, for example, by using an input device, like a keyboard or a mouse, by the user. The user can, for example, choose, whether a selected mark has to be discarded or whether a selected mark has to be accepted. The method of one embodiment is preferentially adapted such that selected marks are discarded and that non-selected marks are accepted. It is further preferred in one embodiment that, after selecting a displayed mark, only non-selected marks are displayed. This allows a user to reduce the number of marks during the review of the marks, in order to decrease the overall number of marks within the image data set, further decreasing the probability of overlooking important marks.

It is also preferred in one embodiment that a displayed mark is provided with a further mark. This can, for example, be performed by inputting the further mark via an input device into an apparatus for displaying marks in an image data set, which performs the method in accordance with one embodiment of the invention. In this case, the image data set comprises the initially provided marks and the later provided added marks. This allows a user, for example, a radiologist, to add further marks to the image data set.

It is further preferred in one embodiment that, if the image data set comprises several images and if a mark is displayed in one of these images, being a first image, in at least one of the other images of the image data set a corridor is displayed, which includes a location, which corresponds to a first location in the first image, which is marked by the mark. This allows a user, like a radiologist, to review corresponding regions in different images, wherein the user is assisted in reviewing a mark displayed in a first image, in particular, in diagnosing, whether a mark displayed in the first image indicates an illness, like cancer or not.

The corridor is preferentially determined by using following steps in one embodiment:
  providing a starting image, being the first image, of an object, and at least one target image of the object, being at least one of the other images,
  providing a second location within the starting image and the at least one target image, being the location of a reference feature detectable in the starting image and in the at least one target image,
  determining a corridor in the at least one target image, wherein the corridor contains a circular line, wherein the circular line defines a circle, whose radius corresponds to a distance between the first location and the second location in the starting image and whose centre position corresponds to the second location,
  presenting the corridor and the at least one target image.

In the starting image and/or in the at least one target image, the object can be deformed, and in each or in some of these images the deformation of the object can be different. Furthermore, the starting image and/or the at least one target image can be a two-dimensional image, like a absorption or transmission projection, for example, a CC image or a MLO image of a breast, or a three-dimensional image, like a three-dimensional computed tomography image or a three-dimensional magnetic resonance image. For example, the starting image and the at least one target image can be two-dimensional images, or one of these images, the starting image or the at least one target image, can be a two-dimensional image, and another image of these images can be a three-dimensional image.

The first location and the second location can be an image point or an extended region within the respective image. Furthermore, since in different images the object can comprise different deformations and can be imaged from different directions, the shape of the first location and/or the second location can differ from image to image. For example, a location, being in the starting image an image point, can be a line in the at least one target image.

The distance between the first location and the second location is preferentially in one embodiment the distance between the centres of these locations. But, the distance can also be any distance between a point at or within the first location and a point at or within the second location.

The circular line can be a complete circular line, e.g., a line forming a circle, or a circular segment line, e.g., a line being a segment of a circle. The corridor is therefore preferentially in one embodiment formed substantially like a ring or like a segment of a ring containing a complete circular line or a circular segment line, respectively. The circular line is preferentially a virtual line in one embodiment, e.g., this circular line is preferentially not displayed in one embodiment.

The centre position of the circle defined by the circular line, e.g., the complete circular line or the circular segment line, is preferentially in one embodiment the centre of the second location in the at least one target image. Alternatively, the centre position of this circle can be any point at or within the second location within the at least one target image.

The circular line defines a circle, whose radius corresponds to the distance between the first location and the second location in the starting image. This means that this radius can be substantially equal to this distance, e.g., it is preferred in one embodiment that a difference length between this radius and this distance is smaller than 10 percent of this distance. It is further preferred in one embodiment that this difference length is smaller than 5 percent of this distance, and it is further preferred in one embodiment that this distance is equal to the radius. That the radius corresponds to the distance also means that, if the object in the at least one target image is magnifiedly shown with respect to the starting image of this object, this radius is substantially equal to an accordingly magnified distance. For example, if the object is magnified by a factor of two in the at least one target image relative to the starting image, the radius is substantially equal to twice a distance between the first location and the second location in the starting image. If the starting image and the at least one target image show the object with different magnifications, the difference between the radius and the accordingly magnified distance is preferentially in one embodiment smaller than 10 percent of the accordingly magnified distance, further preferred in one embodiment smaller than 5 percent of the accordingly magnified distance and further preferred in one embodiment equal to zero.

This embodiment is based on the idea that the first location in the starting image corresponds with a high probability to a region within the at least one target image, which is located within the corridor within the at least one target image. Therefore, the user, like a radiologist, can focus on the corridor, if the user wants to find a region within the at least one target image, which corresponds to the first location within the starting image. The determination of this corridor can be carried out with low computational effort.

This low computational effort is particularly important, if the user is a radiologist and if the images are medical images. A radiologist has to review a large number of medical images in a short time, for example, 200 images in two hours. It is therefore important to determine the corridors very fast, in order to not let a radiologist wait and waist his time.

It is preferred in one embodiment that the object is a breast, wherein the starting image and the at least one target image are medical diagnostic images of the breast, in particular, mammograms, wherein the reference feature is a nipple of a breast. The mammograms are preferably in one embodiment a MLO or ML image and a CC image of the same breast. The deformation of the breast in a MLO or ML image is different to the deformation of the breast in a CC image. Furthermore, the breast in a MLO or ML image has been viewed from another direction than in a CC image. But, although the breast is viewed from different directions and deformed differently, the distance between the first location within the breast and the nipple of the breast being the second location is substantially invariant in the different mammographic views, e.g., this distance does not change very much. It exists therefore a high probability, that a region, which corresponds to a first location in a starting mammogram, is located within the corridor in at least one target mammogram. The presentation method of presenting an image of an object is therefore particularly applicable, if corresponding locations or regions have to be found in different mammograms of the same breast.

The first location is in one embodiment preferentially marked by a CAD mark determined by using a CAD algorithm.

CAD marks are used, in order to help a radiologist to find suspicious regions within a medical image, like a mammogram. A CAD mark marks a region within a mammogram, which is, with respect to the CAD algorithm used by a CAD computer program and/or a CAD device, suspicious of marking an illness, in particular, of marking cancer. If different CAD marks are shown one after another within the image data set in accordance with a generated list, the first location is preferentially in one embodiment the location within an image, being the first image, which is marked by the currently displayed CAD mark. This allows a user to easily review regions, which correspond to the first location, in the at least one target image. Thus, the same region can be viewed in different images of the same object. This improves the review results of a user, like a radiologist.

It is further preferred in one embodiment that the step of providing the second location within the starting image and the at least one target image comprises a step of automatically detecting the second location in at least one of the starting image and the at least one target image. The automatic detection of the second location allows to automatically determine and display the corridor in the at least one target image, if a mark marking a first location in the starting image is displayed.

It is further preferred in one embodiment that the step of providing the second location within the starting image and the at least one target image comprises a step of providing an input unit for inputting the second location within the starting image and the at least one target image. The input unit, for example, a graphical user interface, allows a user to input the second location in the starting image and/or in at least one of the at least one target image. The second location can preferentially be provided in one embodiment within an image by clicking with a mouse pointer on the respective location within the respective image. This allow a user to easily provide the second location in at least one of the starting image and the at least one target image.

It is further preferred in one embodiment that the step of providing the second location within the starting image and the at least one target image comprises a step of providing an input unit for correcting the position of the second location at least within one of the starting image and the at least one target image. The input unit is, for example, a graphical user interface, which allows a user, for example, by using a drag-and-drop operation, to move the second location to another position within the respective image. This allows a user to easily modify the position of a second location which has been provided, for example, by an automatic second location detection system. Such a system is, for example, a nipple detection system using a nipple detection computer program for detecting the nipple of a breast automatically. Such a system is, for example, disclosed in Zhou C, Chan H P, Paramagul C, Roubidoux M A, Sahiner B, Hadjiiski L M, Petrick N, "Computerized nipple identification for multiple image analysis in computer-aided diagnosis", Med Phys. 2004 Oct. 31(10):2871-82.

It is further preferred in one embodiment that the presentation method for presenting an image of an object further comprises the step of providing an input unit for inputting the distance for providing the distance or the step of determining the distance between the first location and the second location in the starting image. Thus, preferentially in one embodiment a user can enter the distance between the first location and the second location in a presentation device for presenting an image of an object in accordance with one embodiment of the invention. For example, if the object is a breast and ultrasound and/or breast magnetic resonance imaging images are present, a user, like a radiologist, can determine the distance between a first location and a second location being the location of the nipple of the breast from the present ultrasound and/or breast magnetic resonance imaging images, and the user can enter this determined distance into the presentation device for presenting an image of an object in accordance with one embodiment of the invention. Thus, the distance between the first location and the second location has not to be determined within the starting image, but this distance can be provided by a user, who knows this distance, for example, from present images of the object, for example, of the breast. This present images can differ from the starting image and the at least one target image. For example, the starting image and the at least one target image can be digital mammograms acquired by a digital mammography device, and the present images, from which the user has determined the distance, can be an image from other modalities, like images from an ultrasound device, a magnetic resonance imaging device or a computed tomography device. However, it is also possible that a user does not enter this distance in the presentation device for presenting an image of an object, but that this distance is determined by the presentation device for presenting an image of an object itself.

It is further preferred in one embodiment that the corridor is determined such that the circular line is located in the middle of the corridor. This leads to a corridor having a high probability of containing a region, which corresponds to the first position, in the at least one target image.

It is further preferred in one embodiment that the first location is extended and that the step of determining the corridor comprises following steps:
  determining the smallest distance and the largest distance between the second location and the extended first location within the starting image,
  determining the corridor such that it contains all image points of the at least one target image having a distance to the second location which is smaller than the largest distance and larger than the smallest distance. This further increases the probability of the corridor of containing a region, which corresponds to a first location within the starting image, within the at least one target image.

It is also preferred in one embodiment that an input unit is provided for inputting a width of the corridor being sufficient to contain all image points of the at least one target image having a distance to the second location which is smaller than the largest distance and larger than the smallest distance. The input unit is preferably a graphical user interface in one embodiment, which allows a user to input a width of the corridor, which is sufficient to contain all image points of the at least one target image having a distance to the second location, which is smaller than the largest distance and larger than the smallest distance. This allows a user to modify the width of the corridor, thus, to further increase the probability of the corridor of containing a region, which corresponds to a first location within the starting image, within the at least one target image by increasing the width of the corridor.

It is further preferred in one embodiment that an input unit is provided for inputting a width value or that a width value is predefined, wherein the corridor is determined such that it contains all image points of the at least one target image having a distance to the second location which is smaller than the largest distance multiplied by the sum of one and the width value and larger than the smallest distance multiplied by the difference between one and the width value. The input unit for inputting a width value is preferably a graphical user interface in one embodiment, which allows a user to input a width value, for example, via a keyboard or a mouse. Since, in this embodiment, the width depends on a fraction of the largest distance and a fraction of the smallest distance, the width of the corridor depends on the distance between the first location and the second location and, thus, a useable width of the corridor can easily be inputted by a user. The width value can also be predefined. If the width value is predefined, the input unit for inputting a width value does not have to be provided. A preferred width value is 25 percent in one embodiment. It is further preferred in one embodiment that the part of the at least one target image, which is located inside of the corridor, is presented more prominent than the part of the at least one target image which is located outside of the corridor. Since the part of the at least one target image, which is located inside of the corridor, is presented more prominent than the part of the at least one target image, which is located outside of the corridor, the user, like radiologist, is focused on the corridor and not distracted by the part of the at least one target image located outside of the corridor. This further increases the assistance of finding corresponding regions in different images.

The part of the at least one target image, which is located outside of the corridor is preferentially in one embodiment shown less prominent by dimming this part. The dimming is preferentially in one embodiment carried out such that the user can still see the outline of the object, in particular, of the breast, in the dimmed part, and that the user can easily focus on the corridor. The dimming is preferentially performed by decreasing the brightness in one embodiment. Alternatively, only the part of the at least one target image can be shown, which is located inside of the corridor, e.g., the part of the at least one target image, which is located outside of the corridor, is, in this embodiment, not shown.

It is further preferred in one embodiment that the image data set comprises a first kind of marks and at least one second kind of marks, wherein during the review phase not all marks of the first kind of marks are displayed at the same time and wherein during the review phase all marks of at least one kind of the at least one second kind of marks are displayed at the same time. Preferentially in one embodiment, during the review phase the marks of the first kind of marks are displayed. Since during the review phase not all marks of the first kind of marks are shown, a user is still less confused by the marks, while, since all marks of at least one kind of the at least one second kind of marks are displayed at the same time, the information from these at least one second kind of marks can also be used during the review phase, which can improve the assistance of a user, like a radiologist, in reviewing marks. For example, if the marks are CAD marks, the first kind of marks are preferentially mass marks in one embodiment, and the at least one second kind of marks are preferentially microcalcification marks in one embodiment In a further aspect of the present invention a method for displaying marks in an image data set is presented, wherein an image data set comprising marks is provided, wherein in an overview phase all marks are displayed, wherein in a review phase the marks are displayed and wherein the overview phase is arranged before and/or after the review phase. This allows a user to have an overview over all marks within the image data set before and/or after the method is performed.

It is further preferred in one embodiment that a selection is performed, wherein an overview phase is arranged after the review phase and wherein in the review phase after the overview phase only non-selected marks are displayed. Since finally only non-selected marks are displayed, marks, which have been selected by the user, in particular, as being of no importance, are not shown, further decreasing the probability of overlooking important marks.

In a further aspect of the invention an apparatus for displaying marks in an image data set is presented, comprising a displaying unit, wherein the apparatus is adapted for displaying not all marks within the image data set at the same time on the displaying unit during a review phase.

It is further preferred in one embodiment that the apparatus comprises a list generation unit for generating a list of the marks by sorting the marks depending on a predetermined sorting criterion and wherein the apparatus unit is adapted for displaying the marks temporally one after another within the image data set in accordance with the generated list during the review phase.

It is further preferred in one embodiment that the image data set is a medical image data set, wherein the marks are CAD marks and wherein the sorting criterion is the probability of marking illness, in particular the suspiciousness.

It is further preferred in one embodiment that the apparatus is adapted for displaying the next mark in the generated list after fulfilling a predetermined switching criterion.

It is further preferred in one embodiment that the apparatus is adapted for displaying an indication indicating the position of the displayed mark within the list and/or the overall number of marks to be displayed.

It is further preferred in one embodiment that the apparatus comprises a list generation unit for generating a list of the marks by sorting the marks depending on a predetermined sorting criterion, wherein the apparatus comprises a grouping unit for grouping the marks into groups wherein each group contains marks being successive in the generated list and wherein the displaying unit is adapted for displaying the groups temporally one after another within the image data set during the review phase. It is further preferred in one embodiment that the image data set is a medical image data set, wherein the marks are CAD marks and wherein the sorting criterion is the probability of marking illness. It is further preferred in one embodiment that the sorting criterion is the suspiciousness. It is further preferred in one embodiment that the apparatus is adapted for displaying the next group after fulfilling a predetermined switching criterion. It is further preferred in one embodiment that the apparatus is adapted for displaying only marks fulfilling at least one given displaying criterion. It is further preferred in one embodiment that the image data set is a medical image data set, wherein the marks are CAD marks and wherein the at least one given displaying criterion is at least one of a microcalcification criterion, a mass criterion and an operating point criterion.

It is further preferred in one embodiment that the displaying unit comprises at least a first display area and a second display area, wherein the apparatus is adapted for displaying in both display areas one or several marks within the image data set and for displaying in the second display area a region around the one or several marks with a larger magnification than in the first display area. It is further preferred in one embodiment that the image data set is a medical image data set and that the marks are CAD marks. It is further preferred in one embodiment that the image data set is a mammogram data set. It is further preferred in one embodiment that the apparatus is adapted for selecting a displayed mark, in particular, to be discarded. It is further preferred in one embodiment that the apparatus is adapted for displaying only non-selected marks, after selecting a displayed mark. It is further preferred in one embodiment that the apparatus is adapted for providing a displayed mark with a further mark.

In a further aspect of the invention an apparatus for displaying marks in an image data set is presented, comprising a displaying unit for displaying the image data set and the marks, wherein the apparatus is adapted for displaying in an overview phase all marks, for displaying in a review phase the marks and for arranging the overview phase before and/or after the review phase. It is preferred in one embodiment that the apparatus is adapted for arranging an overview phase after the review phase and for displaying in the overview phase after the review phase only non-selected marks.

In a further aspect of the present invention an imaging system is presented, comprising:

an image data set generating unit for generating an image data set, a marks generating unit for generating marks depending on the generated image data set, an apparatus for displaying marks within an image data set.

In a further aspect of the present invention computer programs for displaying marks in an image data set are provided.

It shall be understood that the method, the apparatus, the imaging system, and the computer program of the independent claims have corresponding embodiments as defined in the dependent claims.

BRIEF DESCRIPTION OF THE SEVERAL VIEWS OF THE DRAWINGS

These and other aspects of the invention will be apparent from and elucidated with reference to the non-exhaustive and non-limiting embodiments described hereinafter. In the following drawings.

DETAILED DESCRIPTION OF EMBODIMENTS

In the following description, numerous specific details are given to provide a thorough understanding of embodiments. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the claimed invention.

Figure 1:
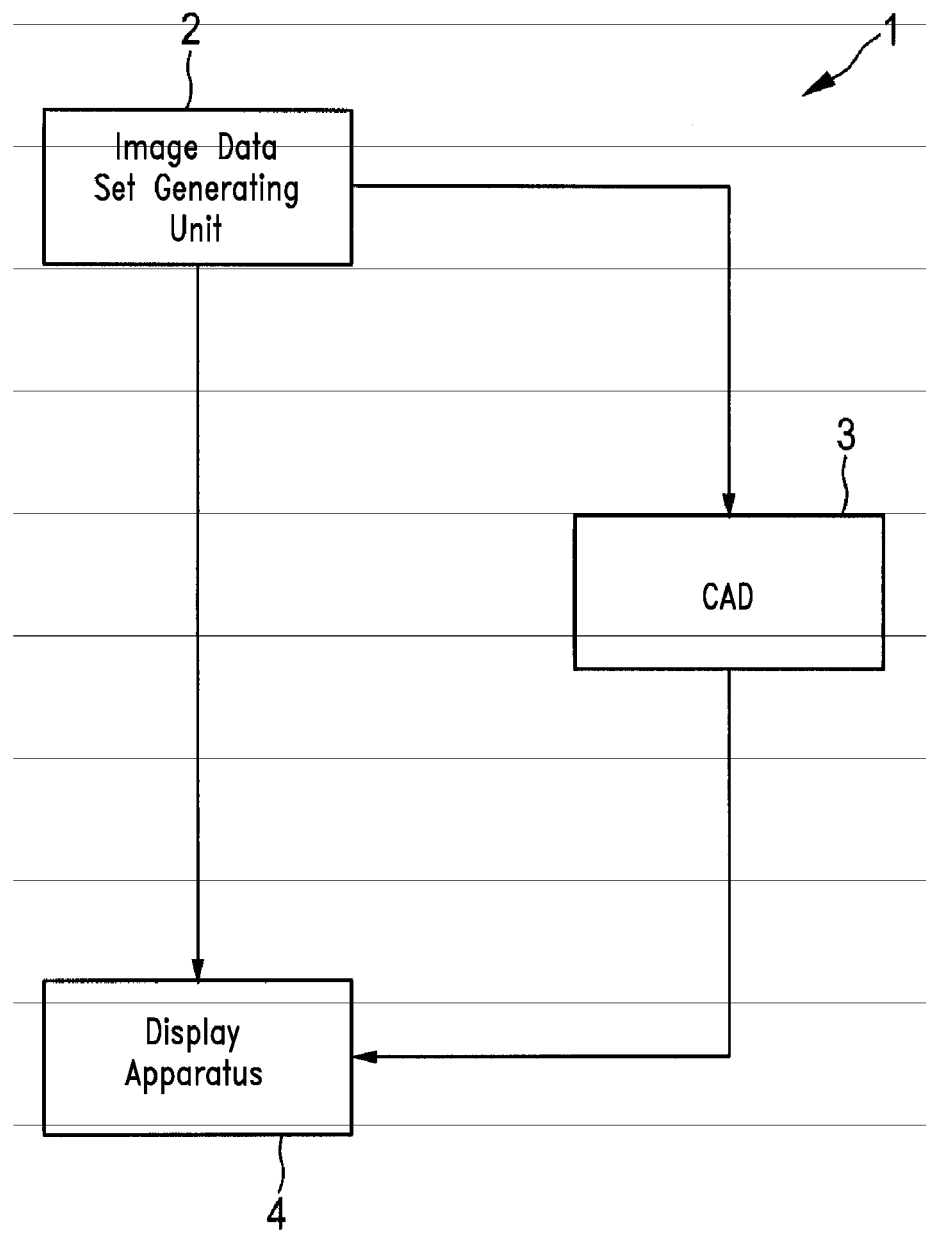
FIG. 1 shows a schematic view of an imaging system in accordance with the invention.

FIG. 1 shows a schematic view of an imaging system 1 comprising an image data set generating unit 2, a CAD mark generation unit 3 and an apparatus for displaying marks in an image data set 4. The image data set generation unit 2 is, for example, a device for acquiring digital mammograms, a computed tomography device, a magnetic resonance imaging device, a tomosyntheses device or any other medical imaging device. The image data set generating unit 2 generates image data sets and transfers them to the CAD mark generating unit 3 and to the apparatus 4 for displaying marks in an image data set. The CAD mark generation unit 3 generates from the image data sets received from the image data set generation unit 42 CAD marks using known CAD algorithms. Such CAD mark generation units 3 and CAD algorithms are, for example, the Image Checker System produced by R2 Technology Inc. and the Second Look Digital System produced by iCAD Inc.

The generated CAD marks are transferred from the CAD mark generation unit 3 to the apparatus 4 for displaying marks in an image data set.

Figure 2:
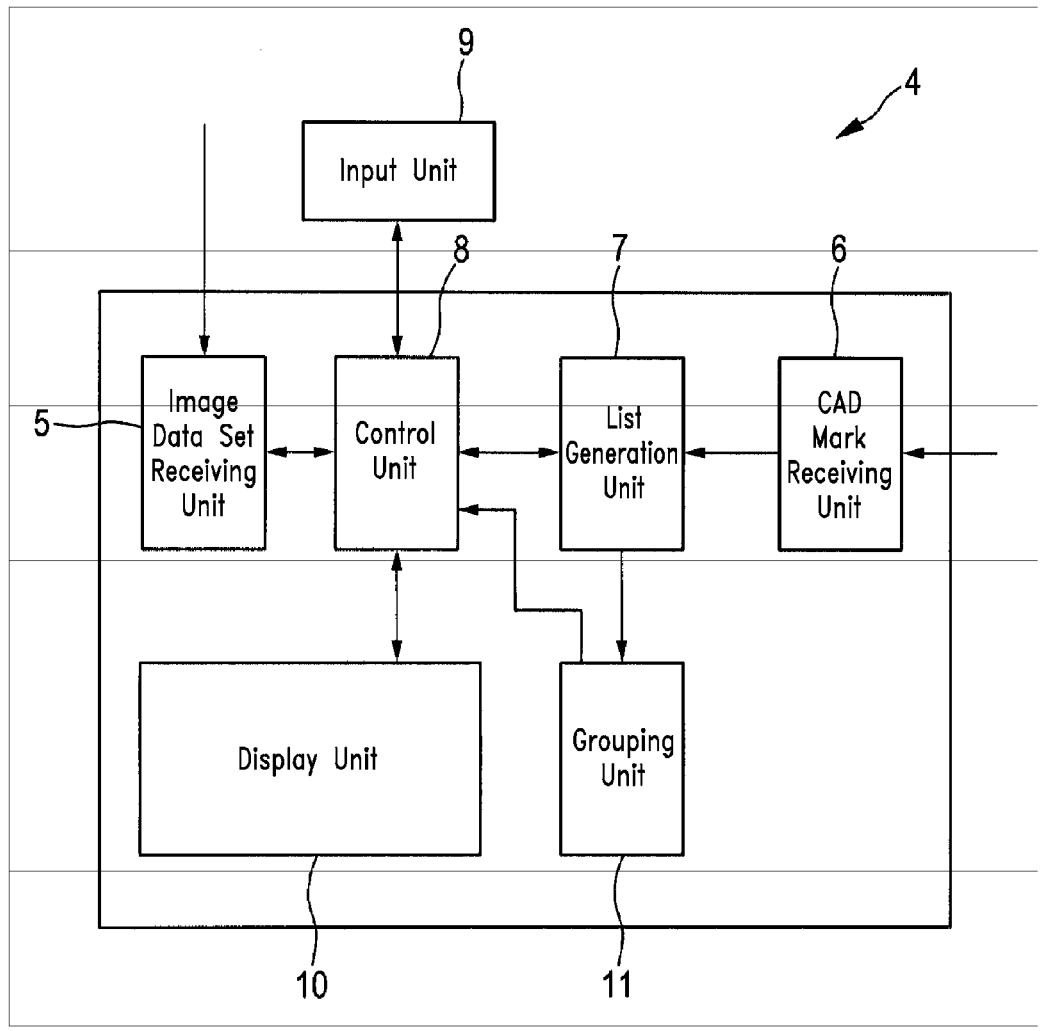
FIG. 2 shows a schematic view of an apparatus for imaging marks within an image data set in accordance with the invention.

The apparatus 4 for displaying marks in an image data set is, in more detail, schematically shown in FIG. 2.

The apparatus 4 for displaying marks in an image data set comprises an image data set receiving unit 5 for receiving image data sets from the image data set generation unit 2. The apparatus 4 comprises further a CAD mark receiving unit 6 for receiving CAD marks from the CAD mark generation unit 3. The CAD marks are preferentially in one embodiment transferred and received in the DICOM format, in particular, as a DICOM CAD Structure Report (SR). The CAD marks, e.g., in particular, the SR, is transferred from the CAD mark receiving unit 6 to a list generation unit 7. The list generation unit 7 can forward the CAD marks to a control unit 8 without modifications, or the list generation unit 7 can generate a list of the marks by sorting the marks depending on a predetermined sorting criterion and the sorted CAD marks can be transferred from the list generation unit 7 to the control unit 8. The control unit 8 receives image data sets from the image data set receiving unit 5 and inputs from an input unit 9. The input unit 9 is, for example, a keyboard or a mouse. The control unit 8 is connected to a display unit 10 for displaying CAD marks and image data sets.

The apparatus 4 for displaying marks in an image data set further comprises a grouping unit 11, which receives sorted CAD marks from the list generation unit 7 for grouping these CAD marks into groups of CAD marks, which are transferred to the control unit 8. The control unit 8 controls the image data set receiving unit 5, the CAD mark receiving unit 6, the list generation unit 7, the input unit 9, the displaying unit 10 and the grouping unit 11 in accordance with a method for displaying marks in an image data set, which will be described further below.

The apparatus for displaying marks in an image data set is preferentially a computer system comprising the different units 5 to 11 in one embodiment. Theses units can be realised by computer programs and/or dedicated hardware. In accordance with one embodiment of the invention, the apparatus for displaying marks in an image data set can also comprise less, additional and/or other units, as long as the apparatus still allows to display not all marks within the image data set at the same time. For example, instead of separate list generation unit 7 and grouping unit 11, a single unit can be used having the same functional features as the list generation unit 7 and the grouping unit 11 together. Furthermore, the image data set receiving unit 5 and the CAD mark receiving unit 6 could be integrated into one receiving unit, which receives both, the image data set and the CAD marks. In addition, the invention is not limited to the data paths within the apparatus 4 for displaying an image data set, which have been described above. For example, the image data sets and CAD marks could be directly transferred to the display unit 10, and not via the control unit 8, while the control unit 8 still controls the data transfer within the apparatus 4 for displaying an image data set.

Figure 3:
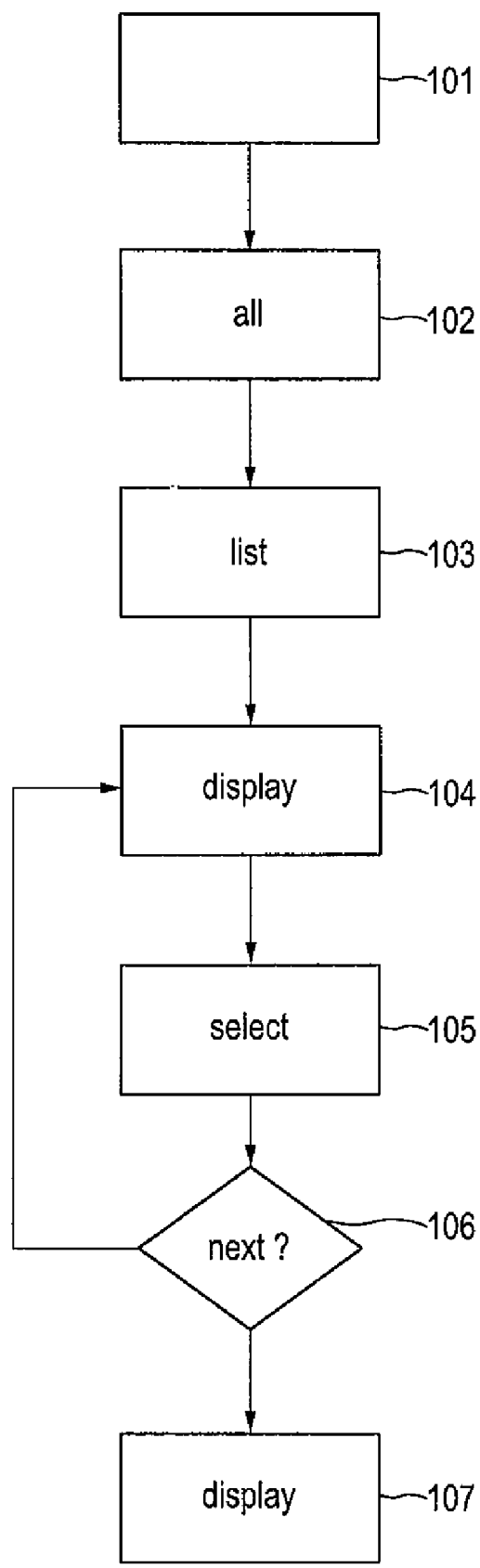
FIG. 3 shows a flow chart of an embodiment of a method for displaying marks within an image data set in accordance with the invention.

An embodiment of a method for displaying marks in an image data set in accordance with one embodiment of the invention will now be described in more detail with respect to a flowchart shown in FIG. 3.

In step 101 the apparatus 4 for displaying marks in an image data set receives an image data set from the image data set generation unit 2 and CAD marks from the CAD mark generation unit 3. In another embodiment, the image data set and the corresponding CAD marks can already be present on the apparatus 4 for displaying marks in an image data set such that an acquisition and/or determination and/or receiving of these data is not necessary. Step 101 would therefore be omitted.

In step 102 the image data set and the CAD marks have been transferred to the displaying unit 10, which displays the image data set and the CAD marks. Such a visualization of the image data set containing the CAD marks can, for example, be performed after a user has requested such a visualization by using the input unit 9. If a user inputs such a request, in this embodiment, the control unit 8 receives this request and controls the displaying unit 10 such that it shows the image data set and the CAD marks, in particular, in an overview phase, all CAD marks, which haven been determined by the CAD mark generation unit 3. In other embodiments, step 102 can be omitted.

Figure 4:
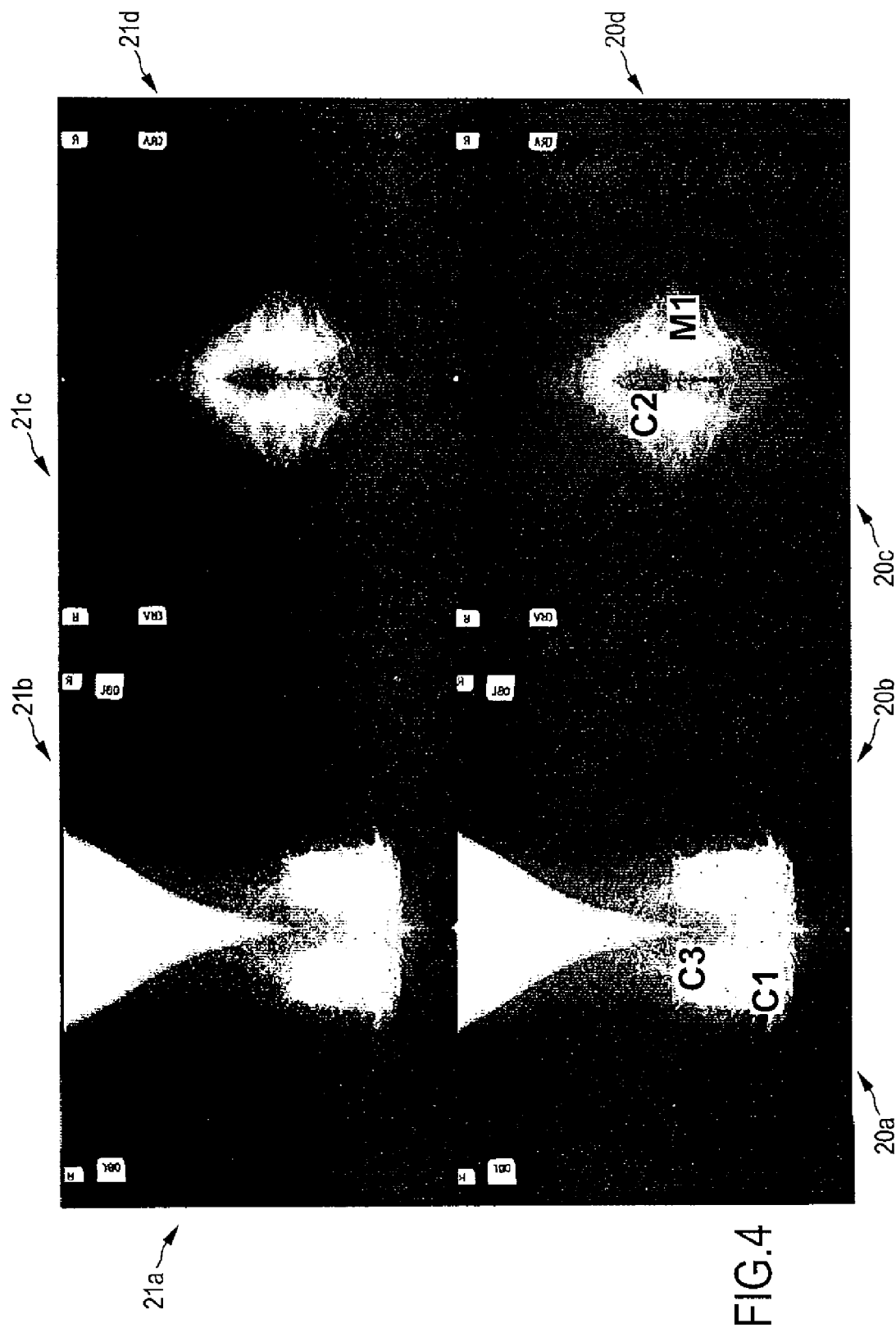
FIG. 4 shows exemplarily an image data set and CAD marks.

A visualization of the image data set and the CAD marks is exemplary shown in FIG. 4. In FIG. 4 digital mammograms $20a, \ldots, 20d, 21a, \ldots, 21d$ are shown. The digital mammograms $20a, \ldots, 20d$ are current mammograms, and the digital mammograms $21a, \ldots, 21d$ are prior mammograms of an earlier examination of the breasts. The digital mammograms $20a, \ldots, 20d$ (for each breast a CC-view image and a MLO-view image) constitute one image data set. Within this image data set four CAD marks C1, C2, C3, M1 are displayed.

In step 103 the list generation unit 7 generates a list of the CAD marks by sorting the marks depending on a predetermined sorting criterion. This sorting criterion is in this embodiment the suspiciousness. The suspiciousness is also known as the certainty of finding. A mark having a large suspiciousness has a large probability of marking illness, in particular, of marking cancer. The suspiciousness is contained in the SR, which has in step 101 been transferred from the CAD mark generation unit 3 to the apparatus 4 for displaying marks in an image data set. Thus, in step 101 a SR has been transferred containing the CAD marks and further information, which is defined in the corresponding DICOM standard. In this exemplary embodiment, the CAD marks' degree of suspiciousness decreases in the following order: C1, M1, C2, C3.

In step 104 the CAD marks are displayed temporally one after another within the image data set on the displaying unit 10 in accordance with the generated list, e.g., in this embodiment, at first the CAD mark C1 is displayed. The displaying unit 10 displays in this embodiment the respective CAD mark on a first display area and on a second display area. In the first display area the respective CAD mark is displayed within a view of the respective image of the image data set showing the whole image containing the respective CAD mark. In the second display area the respective CAD mark is shown in a magnified view. Such a visualization on the displaying unit 10 is exemplarily shown in FIG. 5.

Figure 5:
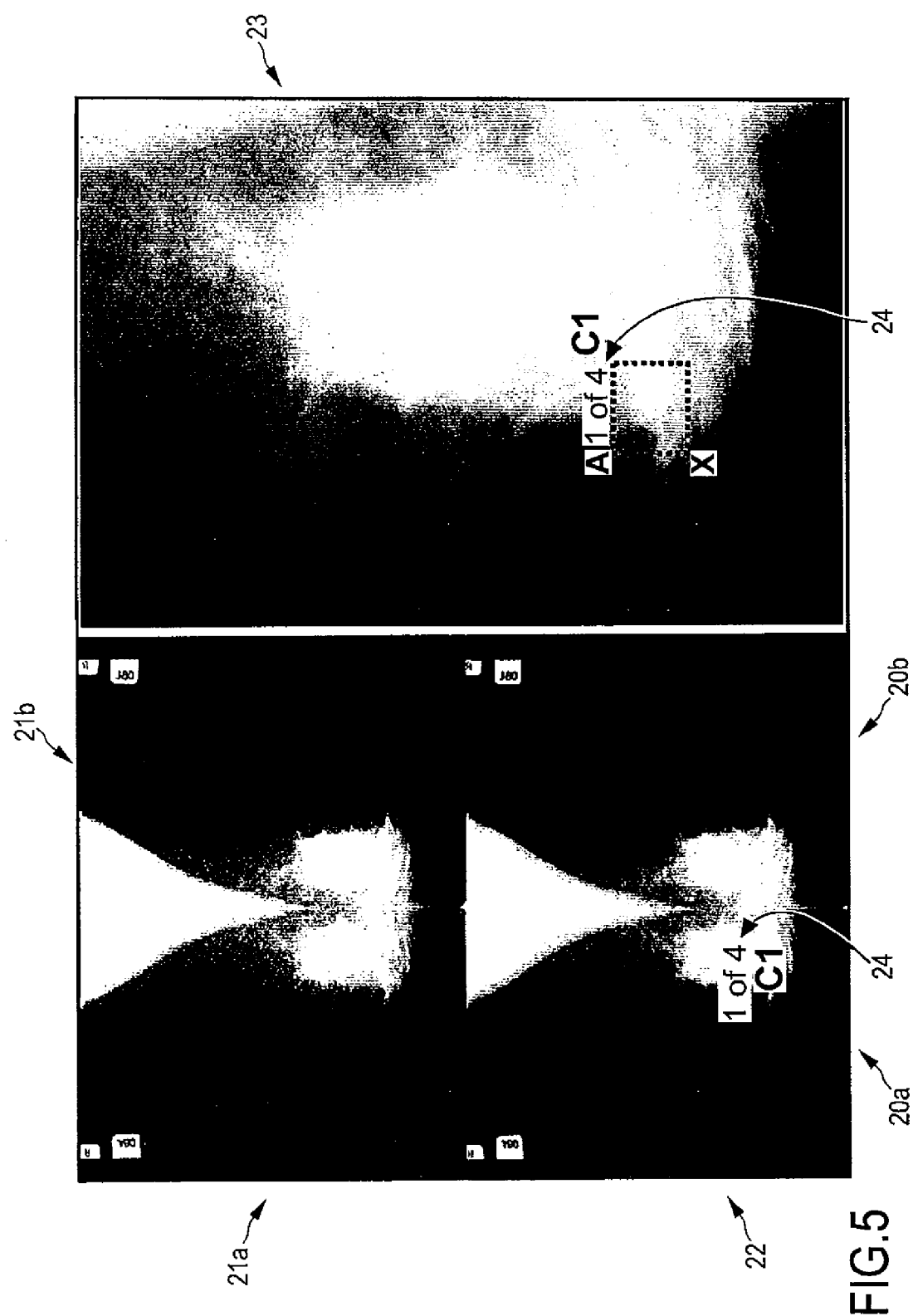
FIG. 5 shows exemplarily an image data set and a CAD mark in a first display area and in a second display area, wherein the CAD mark and the image data set are magnified in the second display area.

FIG. 5 shows two images 20*a*, 20*b* of the current image data set, and images 21*a*, 21*b* of the prior image data set. The, in the generated list, first CAD mark C1 is displayed in a first display area 22 such that substantially the whole corresponding image 20*a* is shown, while in a second display area 23 the CAD mark and the surrounding breast tissue are shown magnifiedly. The first display area 22 and the second display 23 show an indication 24 indicating the position of the displayed CAD mark C1 within the list, which has been generated in step 103.

In step 105 the user has the possibility to select the present CAD mark. In this embodiment, a selected CAD mark is discarded. The selection of a CAD mark can be performed by using the input unit 9.

FIG. 5 shows in the second display area 23 the letters "X" and "A". If the user pushes with a mouse pointer the letter "X" the CAD mark C1 will be selected, e.g., will be discarded, while, if the user pushes with the mouse pointer the letter "A", the CAD mark C1 will be accepted, and preferentially the next mark will be shown in one embodiment. The apparatus 4 for displaying marks in an image data set can also be configured that each non-selected CAD mark is an accepted mark.

In other embodiments in accordance with the invention, step 105 can be omitted.

After the apparatus for displaying marks in an image data set has received a signal from the input unit 9 indicating that the next CAD mark can be displayed, it is determined whether a next CAD mark exists in the list, which has been generated in step 103. If such a next CAD mark exists, the method continues with the next CAD mark with step 104. If a next CAD mark does not exist, all selected CAD marks are displayed on the displaying unit 10 in an overview phase in step 107. Step 107 can be omitted.

The next CAD mark can, for example, be displayed on the display unit 10, if a user pushes with a mouse pointer the letter "A", which is shown in the second display area 23 in FIG. 5.

The steps 103 to 106 define the review phase, during which not all marks within the image data set are displayed at the same time, wherein the attention of the user is focused on the respective CAD mark and wherein, thus, the probability of overlooking an important CAD mark is decreased.

During the method for displaying marks in an image data set a user can add additional marks, which can be displayed within the image data set.

The method for displaying marks within an image data set can be modified such that during performing this method a user can input a signal to the apparatus 4 indicating that now all marks, which have been reviewed and which have not been discarded, shall be shown on the displaying unit 10. The method for displaying marks within an image data set can further be modified such that, after all of these marks have been shown, the method continues, if a further signal is inputted to the apparatus 4 by using the input unit 9 indicating that the review of the marks should continue.

Figure 6:
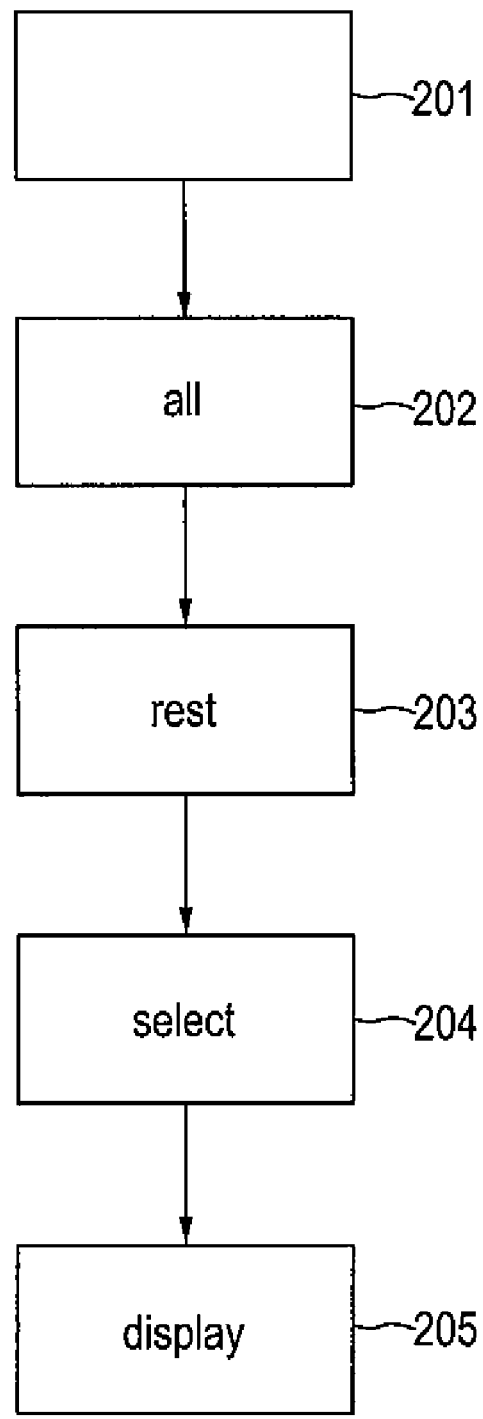
FIG. 6 shows a flowchart of a further embodiment of a method for displaying marks within an image data set in accordance with the invention.

A further embodiment of the method for displaying marks in an image data set in accordance with the invention will in the following be described with reference to a flowchart shown in FIG. 6.

Steps 201 and 202 are identical to steps 101 and 102.

In step 203 only CAD marks are displayed at the same time during the review phase, which fulfil a predetermined displaying criterion. This displaying criterion can, for example, be a microcalcification criterion, a mass criterion or an operating point criterion. The displaying criterion can also be a combination of these criterions. It can be configured, for example, by the user, which of these criterions or which combination of these criterion form the displaying criterion.

Step 204 corresponds to step 105 and can be omitted. Furthermore, as already described in more detail with respect to step 107, in step 205 all marks are displayed within the image data set, which have not been selected, e.g., in this embodiment, which have not been discarded.

Figure 7:
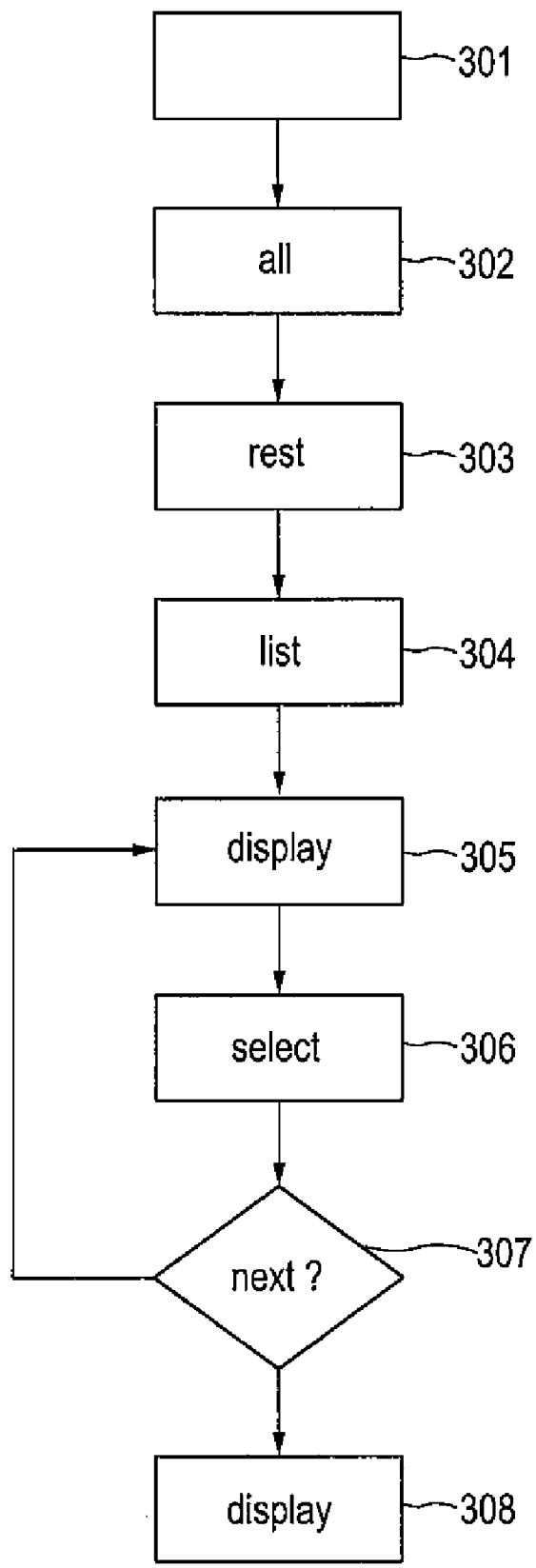
FIG. 7 shows a further embodiment of a method for displaying marks within an image data set in accordance with the invention.

A further embodiment of the method for imaging marks within an image data set in accordance with the invention will in the following be described with respect to a flowchart shown in FIG. 7.

Steps 301 and 302 correspond to steps 101 and 102. In step 303 the CAD marks are restricted as described with respect to step 203. The following steps 304 to 308 are performed only with the CAD marks, which fulfil the displaying criterion of step 303. Except for the restriction to CAD marks, which fulfil the displaying criterion, the steps 304 to 308 correspond to the above described steps 103 to 107. Also step 306 can be omitted.

Figure 8:
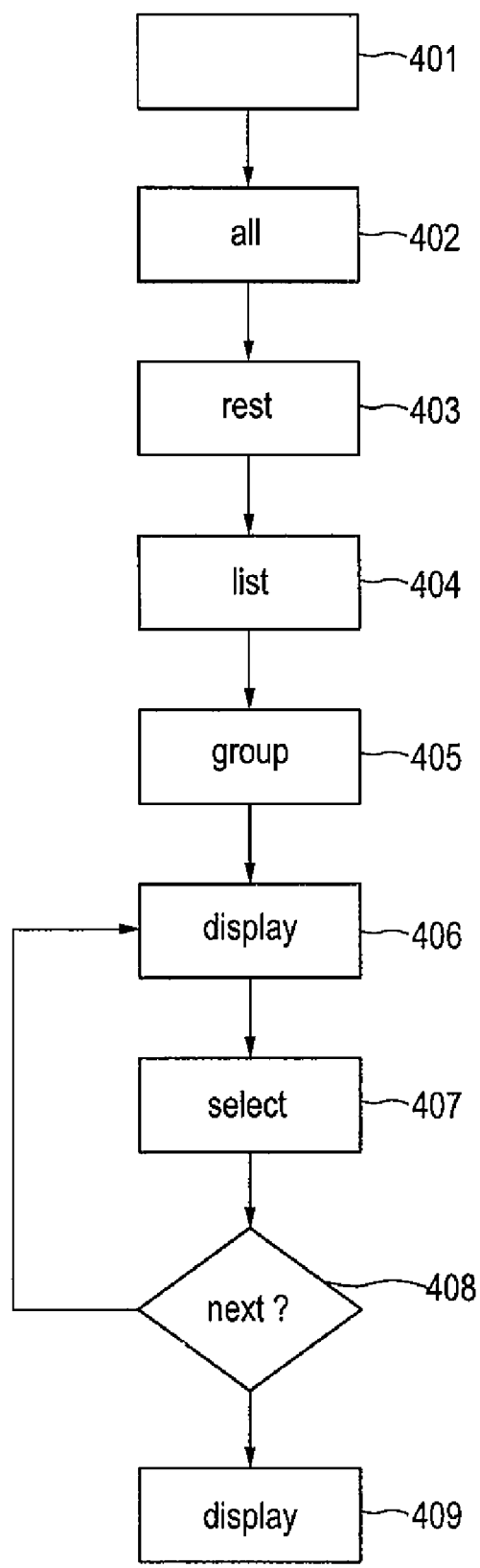
FIG. 8 shows a further embodiment of a method for displaying marks within an image data set in accordance with the invention.

A further embodiment of the method for displaying marks within an image data set will now be described with respect to a flowchart shown in FIG. 8.

Steps 401 and 402 correspond to steps 101 and 102. The restriction in step 403 corresponds to the restriction of step 203. This restriction step 403 can be omitted in this embodiment. The list generation step 404 corresponds to step 103. In step 405 the grouping unit 11 groups CAD marks into groups, wherein each group contains CAD marks being successive in the list, generated in step 404. In the above mentioned example, in which four CAD marks C1, C2, C3, M1 are present within the image data set, a first group could contain the marks C1, M1 and a second group could contain the marks C2, C3. The steps 406 to 408 correspond to steps 104 to 106, except for the difference that in step 406 all marks of the group are displayed at the same time and that, in step 408, it is checked, whether a next group exists. Step 409 corresponds to step 107.

The order of the above described steps is not strict. For example, the viewing step 102, 202, 303, the restriction step 203, 303 and the list generation step 103, 304 can be mixed in the respective flowcharts shown in FIGS. 3, 6 and 7, if present.

If the image data set comprises several images and if a mark is displayed in one of these image, being a first image, in at least one of the other images, being at least one target image, of the image data set a corridor is in one embodiment preferentially displayed, which includes a location, which corresponds to the location in the starting image, which is marked by the respective mark.

If the display criterion is an operating point criterion, preferentially only CAD marks are displayed in one embodiment, which correspond to a given operating point. This operating point can be entered into an apparatus for displaying marks in an image data set, for example, by using a graphical user interface comprising a sliding scale, wherein, preferentially in one embodiment, by using the sliding scale one of three operating points can be selected.

The sorting criterion and/or the displaying criterion can also be a value, which is or depends on the architectural noise. The architectural noise is related to the probability of marking illness, in particular, the probability of marking cancer. The architectural noise can be formed by a seemingly random pattern, which is formed by various tissues in the breast (ducts, lobules and connective tissue). In the science of image analysis there are various measures for noise (entropy, Fourier power spectrum, fractal dimension, etc.). In combination with some image processing, such as edge enhancement, and enhancement of linear structures etc., this mathematical concepts can be used to quantify the architectural noise in mammograms.

Although some embodiments of the invention, which have been described above, use CAD marks, these embodiments are not limited to a certain CAD mark generation unit. These embodiments can be performed independent of the respective CAD mark algorithm used by the CAD mark generation unit. These embodiments only require CAD marks, but it is not important how these CAD marks have been determined.

While one or more embodiments of the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

It is apparent for a skilled person that the features of the dependent claims can be combined and added to the corresponding independent claims.

U.S. application Ser. No. 11/465,078, entitled "METHOD, APPARATUS AND COMPUTER PROGRAM FOR PRESENTING CASES COMPRISING IMAGES," filed Aug. 16, 2006, with inventors Dr. Carl J. G. Evertsz and Dr. Anke Bödicker; and U.S. application Ser. No. 11/465,074, entitled "PRESENTATION METHOD, PRESENTATION DEVICE AND COMPUTER PROGRAM FOR PRESENTING AN IMAGE OF AN OBJECT," filed Aug. 16, 2006, with inventors Dr. Carl J. G. Evertsz and Dr. Anke Bödicker, both provide additional disclosure and are incorporated herein by reference in their entireties.

All of the U.S. patents, U.S. patent application publications, U.S. patent applications, foreign patents, foreign patent applications and non-patent publications referred to in this specification and/or listed in the Application Data Sheet are incorporated herein by reference, in their entirety

The invention claimed is:

1. A method for displaying marks in an image data set having marks, wherein during a review phase not all marks within the image data set are displayed at a same time, the method comprising:
   under control of an apparatus configured for displaying the marks within the image set for review,
      generating a list of the marks by sorting the marks depending on a sorting criterion, wherein the sorting criterion is a probability of marking illness, including suspiciousness;
      grouping the marks into groups, wherein each group includes marks that are successive in the generated list, and wherein at least one of the groups includes a plurality of marks that have different probabilities of marking illness; and
      displaying the groups temporally one after another within the image data set during the review phase, wherein marks of a group are displayed at a same time,
      wherein the image data set includes a medical image data set and wherein the marks include computer-aided detection (CAD) marks.

2. The method as claimed in claim 1, wherein an indication is displayed indicating a position of a displayed mark within the list and/or an overall number of marks to be displayed.

3. The method as claimed in claim 1, wherein a next group is displayed after fulfilling a switching criterion.

4. The method as claimed in claim 1, wherein only marks are displayed at a same time during the review phase fulfilling at least one given displaying criterion.

5. The method as claimed in claim 4, wherein the at least one given displaying criterion includes at least one of a microcalcification criterion, a mass criterion and an operating point criterion.

6. The method as claimed in claim 4, wherein an input device is provided to enter at least one displaying criterion as the at least one given displaying criterion in an apparatus adapted to display marks in the image data set.

7. The method as claimed in claim 1, wherein the marks are displayed at least in a first display area and in a second display area, wherein in both display areas one or several marks are displayed within the image data set and wherein in the second display area a region around the one or several marks is displayed with a larger magnification than in the first display area.

8. The method as claimed in claim 1, wherein the image data set includes a mammogram data set.

9. The method as claimed in claim 1, wherein a displayed mark is selectable to be discarded.

10. The method as claimed in claim 9, wherein after selecting a displayed mark, only non-selected marks are displayed.

11. The method as claimed in claimed 1, wherein a displayed mark is provided with a further mark.

12. The method as claimed in claim 1, wherein, if the image data set includes several images and if a mark is displayed in one of these images, being a first image, in at least one of the other images of the image data set a corridor is displayed, which includes a location, which corresponds to a first location in the first image, which is marked by the mark.

13. The method as claimed in claim 1, wherein the image data set includes a first kind of marks and at least one second kind of marks, wherein during the review phase not all marks of the first kind of marks are displayed at a same time and wherein during the review phase all marks of at least one kind of the at least one second kind of marks are displayed at a same time.

14. A method for displaying marks in the image data set having marks, wherein in an overview phase all marks are displayed, wherein in the review phase the marks are displayed as defined in claim 1 and wherein the overview phase is arranged before and/or after the review phase.

15. The method as claimed in claim 14, wherein a selection is performed to discard a displayed mark, wherein the overview phase is arranged after the review phase and wherein in the overview phase after the review phase only non-selected marks are displayed.

16. An article of manufacture, comprising:
   a hardware storage medium having stored thereon a computer program to display marks in an image data set, the computer program having program code to cause a computer to carry out the method as claimed in claim 14 when the computer program is carried out on said computer, which is adapted to control an apparatus to display the marks in the image data set, the apparatus including a display unit to display the image data set and the marks, wherein the apparatus is adapted to display in said overview phase all marks, to display in said review phase not all marks within the image data set at a same time, and to arrange the overview phase before and/or after the review phase.

17. An apparatus to display marks in the image data set, comprising a displaying unit to display the image data set and the marks, wherein the apparatus is adapted to display in an overview phase all marks, to display in the review phase the marks as defined in claim 1 and to arrange the overview phase before and/or after the review phase.

18. An article of manufacture, comprising:
   a hardware storage medium having stored thereon a computer program to display marks in the image data set, the computer program having program code to cause a computer to carry out the method as claimed in claim 1 when the computer program is carried out on said computer, which is adapted to control an apparatus to display the marks in the image data set, the apparatus including a display unit, wherein the apparatus is adapted to display not all marks within the image data set at a same time on the display unit during the review phase.

19. The method of claim 1 wherein by displaying said marks of said group at the same time, several of said marks, which might be similar with respect to the sorting criterion, are enabled to be reviewed at the same time so as to increase speed of reviewing, while since said marks of said group and not all marks are displayed at the same time, user confusion by an amount of marks displayed at the same time is reduced.

20. The method of claim 1 wherein by sorting the marks depending on said probability of marking illness, including suspiciousness and wherein by displaying the groups temporally one after another within the image data set during the review phase and wherein by displaying said marks of said group at the same time, the marks are presentable to a user in accordance with a level of attention of the user, such that marks with highest probability of marking illness are shown when the user has highest attention level so as to decrease a probability of overlooking important marks.

21. An apparatus to display marks in an image data set, comprising:
   a display unit, wherein the apparatus is adapted to display not all marks within the image data set at a same time on the display unit during a review phase;
   a list generation unit to generate a list of the marks by sorting the marks based on a sorting criterion, wherein the sorting criterion is a probability of marking illness, including suspiciousness; and
   a grouping unit to group the marks into groups,
   wherein each group includes marks that are successive in the generated list, wherein at least one of the groups includes a plurality of marks that have different probabilities of marking illness, and wherein the display unit is adapted to display the groups temporally one after another within the image data set during the review phase, and wherein marks of a group are displayed at a same time, and
   wherein the image data set includes a medical image data set and wherein the marks include computer-aided detection (CAD) marks.

22. The apparatus as claimed in claim 21, wherein the apparatus is adapted to display only marks fulfilling at least one given displaying criterion.

23. An imaging system comprising:
   an image data set generating unit to generate the image data set;
   a marks generating unit to generate marks depending on the generated image data set; and
   the apparatus to display marks within the image data set as defined in claim 21.

* * * * *